United States Patent
Estrada, Jr.

(10) Patent No.: US 11,246,735 B2
(45) Date of Patent: Feb. 15, 2022

(54) CONFORMING RIGID CAST, BRACE AND SPLINT COMPRISING A CURABLE POLYMERIC MATERIAL

(71) Applicant: H. Mark Estrada, Jr., Lakeway, TX (US)

(72) Inventor: H. Mark Estrada, Jr., Lakeway, TX (US)

( * ) Notice: Subject to any disclaimer, the term of this patent is extended or adjusted under 35 U.S.C. 154(b) by 222 days.

(21) Appl. No.: 15/857,502

(22) Filed: Dec. 28, 2017

(65) Prior Publication Data

US 2018/0168843 A1 Jun. 21, 2018

Related U.S. Application Data

(63) Continuation-in-part of application No. 15/195,917, filed on Jun. 28, 2016, now abandoned.

(51) Int. Cl.
*A61F 13/04* (2006.01)
*A61F 5/058* (2006.01)
*A61F 5/02* (2006.01)

(52) U.S. Cl.
CPC .............. *A61F 5/058* (2013.01); *A61F 5/022* (2013.01); *A61F 5/024* (2013.01); *A61F 13/04* (2013.01)

(58) Field of Classification Search
CPC ...... A61F 5/0106; A61F 5/022; A61F 5/0585; A61F 13/01; A61F 5/02; A61F 5/058; A61F 5/05825; A61F 5/05833; A61F 13/04; A61F 5/05866
See application file for complete search history.

(56) References Cited

U.S. PATENT DOCUMENTS

| | | | | |
|---|---|---|---|---|
| 2,077,299 A | * | 4/1937 | Abrams | A61L 15/34 604/304 |
| 3,656,475 A | * | 4/1972 | Hanrahan, Jr. | A61F 13/04 602/8 |
| 3,930,496 A | * | 1/1976 | Gibbons | A61F 13/04 602/8 |
| 4,628,917 A | * | 12/1986 | Campagna, Jr. | A61L 15/07 602/8 |
| 4,793,330 A | * | 12/1988 | Honeycutt | A61F 13/04 523/105 |

(Continued)

OTHER PUBLICATIONS

Jimenez, "Total Contact Casting," Chapter 51, pp. 282-287, downloaded from <http://www.podiatryinstitute.com/pdfs/Update_2003/2003_51.pdf>. on Sep. 29, 2021, 2003.

*Primary Examiner* — Camtu T Nguyen
(74) *Attorney, Agent, or Firm* — Gregory K. Goshorn; Greg Goshorn, P.C.

(57) ABSTRACT

A formable cast (100), brace (180) or splint is provided herein which comprises a padding (101), an outer shell (103) spaced apart from the padding, and a ridge (109) disposed along the perimeter of the shell. The ridge, shell and padding define an interior space (115), with a curable polymeric material disposed in the interior space. The curable polymeric material undergoes a phase transition, upon curing, from a liquid or gel phase to a substantially rigid solid phase. The cast (100), brace (180) or splint may be readily customized to the patient by fitting the cast to the patient's body, positioning the cast in the desired orientation, and curing the curable polymeric material through exposure to actinic radiation or by other suitable means.

18 Claims, 6 Drawing Sheets

(56) References Cited

U.S. PATENT DOCUMENTS

| | | | | |
|---|---|---|---|---|
| 5,085,210 | A * | 2/1992 | Smith, III | A61F 5/0123 |
| | | | | 602/26 |
| 5,480,376 | A * | 1/1996 | Duback | A41D 13/015 |
| | | | | 602/8 |
| 5,632,723 | A * | 5/1997 | Grim | A61F 5/022 |
| | | | | 602/19 |
| 6,152,892 | A * | 11/2000 | Masini | A61F 5/0104 |
| | | | | 128/846 |
| 6,893,410 | B1 | 5/2005 | Hely | |
| 7,004,917 | B2 * | 2/2006 | Henderson | A61F 13/04 |
| | | | | 602/5 |
| 7,037,283 | B2 * | 5/2006 | Karason | A61F 13/041 |
| | | | | 602/5 |
| 8,147,438 | B2 | 4/2012 | Livolsi et al. | |
| 2005/0240140 | A1 | 10/2005 | Nelson et al. | |
| 2007/0207186 | A1 * | 9/2007 | Scanlon | A61F 2/91 |
| | | | | 424/424 |
| 2009/0171356 | A1 * | 7/2009 | Klett | A61B 90/98 |
| | | | | 606/54 |
| 2009/0294692 | A1 * | 12/2009 | Bourke, Jr. | A61L 2/0047 |
| | | | | 250/459.1 |
| 2010/0311861 | A1 * | 12/2010 | Clapper | C08G 18/73 |
| | | | | 522/167 |
| 2015/0250636 | A1 * | 9/2015 | Darcey | A61F 5/058 |
| | | | | 602/5 |

\* cited by examiner

CONFORMING RIGID CAST, BRACE AND SPLINT COMPRISING A CURABLE POLYMERIC MATERIAL

CROSS-REFERENCES TO RELATED APPLICATIONS

The present application is a continuation-in-part and claims the benefit of the filing date of an application entitled, "Conforming Rigid Cast and Brace Comprising a Curable Polymeric Material" Ser. No. 15/195,917 filed Jun. 28, 2016, assigned to the assignee of the present application, and herein incorporated by reference.

FIELD OF THE DISCLOSURE

The present invention relates generally to medical casts, braces and splints, and more specifically, to methods of creating and affixing a protective medical cast or brace that comprises a curable polymeric material.

BACKGROUND

Bone fractures are a common result of blunt trauma and other types of accidents. A fracture occurs when sufficient force is applied to a bone such that the bone chips, cracks, or breaks. Once a fracture is diagnosed, the pieces or fragments of the broken bone are properly realigned by medical personnel through a process called reduction. The pieces are then held in position by means of a splint, cast, brace, or traction to allow them to properly fuse together during the healing process. In addition to maintaining the bone fragments in proper alignment, a cast, splint or brace may serve to decrease pain, keep surrounding tissue from becoming damaged, reduce the chance of serious bleeding and lost circulation to the injured part, and prevent movement, and perhaps re-injury, of the fractured bone during the healing process.

For many years, casts were made of plaster and cloth, or "padding." Typically, the plaster for such casts comes in strips or rolls which are dipped in water and applied over the padding. The padding itself is usually a layer of cotton or synthetic fiber that covers the injured area. Once watered and positioned, the plaster is allowed to harden or cure. While the plaster cures, the patient must remain still so that the resultant cast can set into its proper shape. This method of treating a broken bone in this manner is both messy for the health care provider and inconvenient for the patient. In addition, a plaster cast is heavy and, as a result, unwieldy through out the healing process, which typically last eight through ten weeks.

In some casts, the plaster may be replaced with fiberglass. Fiberglass is lighter, longer wearing, and provides better ventilation than plaster. It is also more transparent to x-rays, thus allowing the medical personnel to easily monitor the healing process. However, fiberglass casts are generally more expensive than plaster casts, are often equally difficult and messy to work with, and still require the use of padding material. As with plaster, fiberglass comes in strips or rolls which are dipped in hot water and applied over the padding that covers the injured area.

In addition to casts, other types of protective shells and braces have found use in medical applications. Examples include braces of the type that are commonly used to treat back and knee injuries or conditions and splints used to treat broken bones. For example, back braces have been developed that are designed to compress and unload weight from the lumbar region of a patient's back. These braces fall into two general categories, Lumbosacral Orthosis (LSO) braces and Thoracic Lumbosacral Orthosis (TLSO) braces. These braces may include posterior and/or anterior protective shells. Both the anterior and posterior shells are typically constructed of light-weight, inexpensive thermoplastics.

Currently, braces and splints are either dispensed in a limited number of sizes and shapes, or are custom manufactured using expensive and time-consuming procedures. Braces that are sold in a limited number of sizes (so called "off-the-shelf" braces) suffer from the infirmity that they can not be fitted as precisely as a custom brace, and are thus less comfortable and effective in use. Custom braces and splints overcome this infirmity, but are typically much more expensive and time consuming to fabricate than off-the-shelf braces and splints of the type that can be made using economies of scale. In particular, custom braces and splints may cost thousands of dollars to produce, and may take weeks to fabricate.

SUMMARY

In accordance with the teachings herein, casts, braces splints, and related medical devices are provided that can be conveniently and inexpensively customized to the patient, that are not messy to apply, that are light-weight and wear-resistant, and that have good breathability. These devices are suitable for treating bone fractures, for providing support, and for other medical applications. Systems and methods for fabricating these devices are also provided.

As the Inventors herein have realized, there is thus a need in the art for casts and braces that can be conveniently and inexpensively customized to the patient, that are not messy to apply, that are light-weight and wear-resistant, and that have good breathability. These and other needs are met by the systems, devices and methodologies disclosed herein.

Although the devices, systems and methodologies disclosed herein will frequently be described in the context of treating bone fractures, and in particular, broken arms, these devices and methodologies are equally applicable to any type of situation in which a cast is required. In addition, the methods and devices described herein are not restricted to human applications, but may also be applied in the veterinary arts.

Briefly, a method is provided herein in which an encased, curable (preferably photocurable) cast, brace or splint material is wrapped around a body part such as, but not limited to, a broken arm. Once the curable cast, brace or splint material is positioned and shaped, an actinic radiation source, such as, but not limited to, an ultraviolet (UV) light source, is applied to the cast, brace or splint material. The radiation emitted by the actinic radiation source reacts with the cast, brace or splint material, causing it to cure or harden. Unlike plaster or fiberglass cast, brace and splint materials, the radiation curable cast, brace and splint materials described herein can be positioned and shaped for an indefinite period of time because the material does not begin to harden until exposed to the actinic radiation source. In addition, the rate at which the cast, brace and splint material hardens can be controlled by varying the conditions of exposure, including, but not limited to, the intensity and wavelengths of the actinic radiation source. Using a typical UV light source, a cast, brace or splint can be made in accordance with the teachings herein that may cure in as little as five seconds or less.

In addition, the systems and methods disclosed herein may be employed to produce custom-fitted medical braces, such as back and knee braces, and splints. In contrast to conventional braces, which are very expensive and typically take several weeks to fit and fabricate, customized braces may be made in accordance with the methodologies disclosed herein that are ready for use concurrently with the fitting procedure. This greatly reduces the inconvenience to the patient, and avoids further injury that might otherwise occur while the patient is waiting for the brace or splint to be prepared.

This summary is not intended as a comprehensive description of the claimed subject matter but, rather, is intended to provide a brief overview of some of the functionality associated therewith. Other systems, methods, functionality, features and advantages of the invention will be or will become apparent to one with skill in the art upon examination of the following figures and detailed description.

BRIEF DESCRIPTION OF THE DRAWINGS

The invention can be better understood with reference to the following figures. The components in the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS

In the ensuing detailed description, the systems, methodologies and devices disclosed herein will frequently be described with reference to particular embodiments, such as back braces, knee braces and casts, and with respect to particular applications, such as the treatment of broken bones in the arms or legs. However, it will be appreciated that the systems, methodologies and devices disclosed herein may be implemented in a variety of embodiments and applications. Moreover, while the systems, methodologies and devices disclosed herein will be described primarily with reference to their use in human medical applications, it will be appreciated that these systems, methodologies and devices will also find use in various other fields, such as the veterinary arts.

Figure 1:
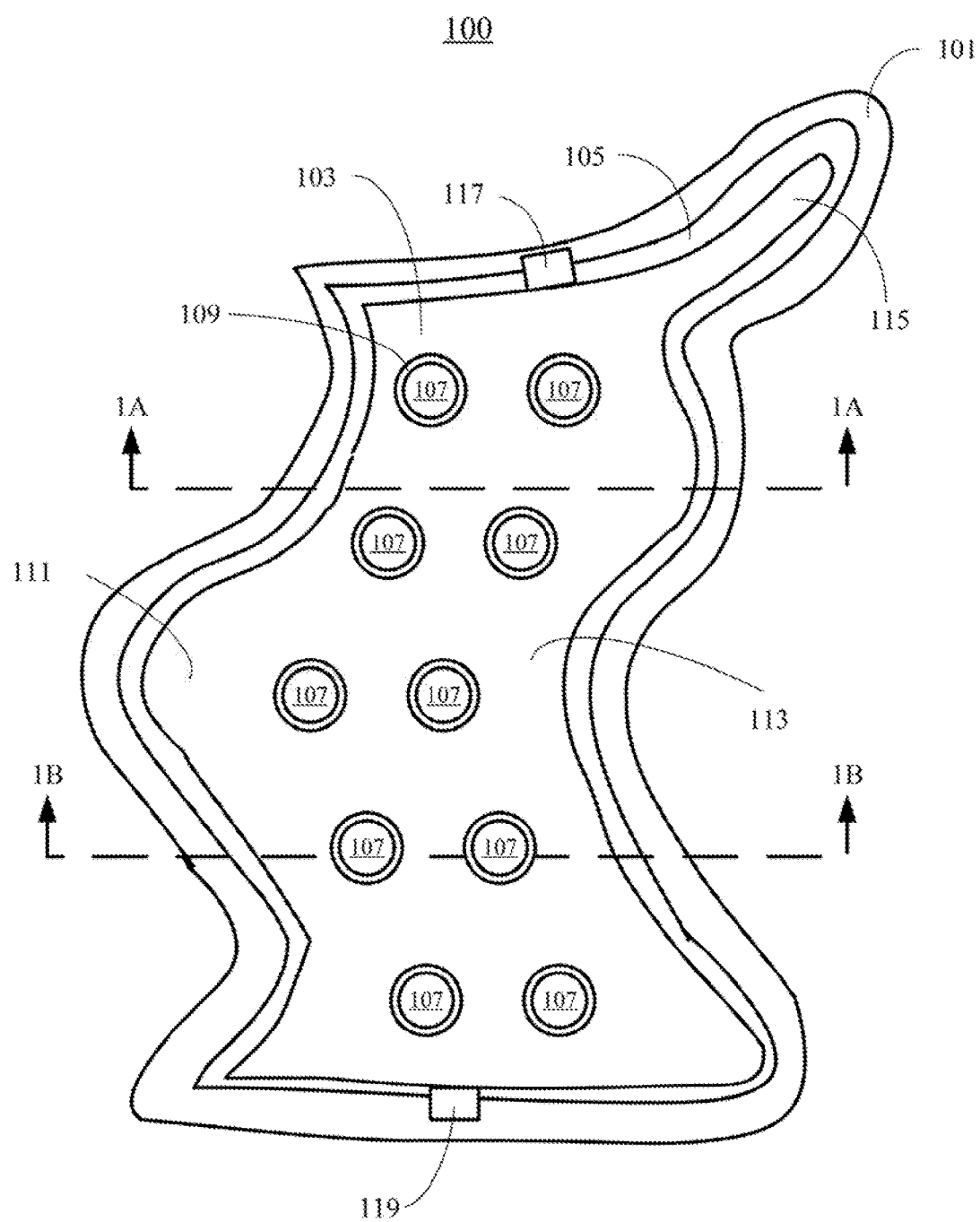
FIG. 1 is an illustration of an exemplary arm cast system constructed in accordance with the claimed subject matter.

FIG. 1 illustrates one embodiment of an arm cast system 100 which may be constructed in accordance with the claimed subject matter. A bottom portion or pad 101 is provided which is preferably constructed of a breathable, resilient material, such as GORETEX® neoprene, and which allows air to permeate to the injured area while also protecting the area from other, perhaps harder portions of cast system 100. Pad 101 also serves, if necessary, to insulate a patient from heat produced by the curing of cast system 100. A top portion 103 is provided which is constructed of a flexible material such as standard, medical grade silicon. In an alternative embodiment, pad 101 is made of the same material as top portion 103, and a separate padding material is used beneath cast system 100. It should be noted that pad 101 may extend from one side of top portion 103 to the other side, i.e., pad 101 includes material beneath top portion 103. In this view, pad 101 extends out from the edges of top portion 103. In an alternative embodiment, pad 101 may have the same approximate size and shape as top portion 103 so that pad 101 does not extend past the edge of top portion 103.

The perimeter of top portion 103 of the cast system 100 is equipped with a ridge 105. The top portion 103 and ridge 105 are preferably fabricated as a single piece of flexible material, though in some embodiments top portion 103 and ridge 105 may be fabricated separately or as distinct components. Thus, for example, ridge 105 may be fabricated as a distinct component similar to a gasket. Top portion 103 and pad 101 are affixed to each other along the length of ridge 105. This may be accomplished by means of a suitable adhesive, by thermally bonding the materials together, or through other suitable means as are known to the art. One skilled in the art will appreciate that the choice of a suitable adhesive for attaching pad 101, top portion 103 and ridge 105 may vary, and may depend on such factors as the specific materials employed in the manufacture of pad 101, top portion 103 and ridge 105. Ridge 105 is sufficiently raised from top portion 103 such that there is a gap 131 (see FIGS. 2 and 3) between top portion 103 and pad 101. As explained in greater detail below in conjunction with FIGS. 2 and 3, gap 131 is preferably filled with a radiation curable or energy-sensitive material, such as a polyurethane- or polyacrylate-based resin.

In this embodiment, top portion 103 has ten (10) holes 107, each of which is surrounded by a corresponding ridge 109. Ridges 109 are approximately the same height as a ridge 105 and also are affixed to pad 101. In this manner, the radiation curable or energy curable resin that fills gap 131 does not leak out through holes 107. Holes 107 are designed to enable cast system 100 to breath, and thus increase the comfort to a patient employing cast system 100. The precise arrangement, size and number of holes 107 may vary. In an alternative embodiment, pad 101 is also cut out in areas corresponding to holes 107 such that holes 107 extend through both pad 101 and top portion 103.

Pad 101 and top portion 103 are contoured such that portions are convex and concave in corresponding portions of opposing sides of pad 101 and top portion 103, e.g. e.g. a convex portion 111 and a concave portion 113. When cast system 100 is wrapped around a patient's limb, convex portion 111 fits into concave portion 113. This positioning is shown in more detail below in conjunction with FIG. 5. In alternative embodiments, cast system 100 may have multiple convex and corresponding concave portions, or simply have a straight edge.

A portion of pad 101 and top portion 103 also extend outward in a finger-like extension 115. Extension 115 is configured, in the context of an arm cast such as cast system 100, to extend between the patient's thumb and first finger when cast system 100 is positioned on the patient's arm. Extension 115 helps cast system 100 from moving relative to the patient's arm once cast system 100 has been positioned on the patient's arm and hardened. The relative position of extension 115 with respect to cast system 100 and an exemplary patient's arm are shown in more detail below in conjunction with FIG. 5.

Cast system 100 also includes one or more radiation access channels 117 and 119, each of which is constructed of a transparent material through which radiation for curing the energy sensitive material that fills gap 131 can pass. Radiation access channels 117 and 119 are positioned on top of pad 101 and extend through ridge 105.

Also shown in FIG. 1 are dotted lines 1A-1A and 1B-1B. Lines 1A-1A and 1B-1B are not actually part of cast system 100, but rather are used to provide points of reference in cast system 100 corresponding to the cross-sectional views illustrated in FIGS. 2 and 3, respectively.

Figure 2:
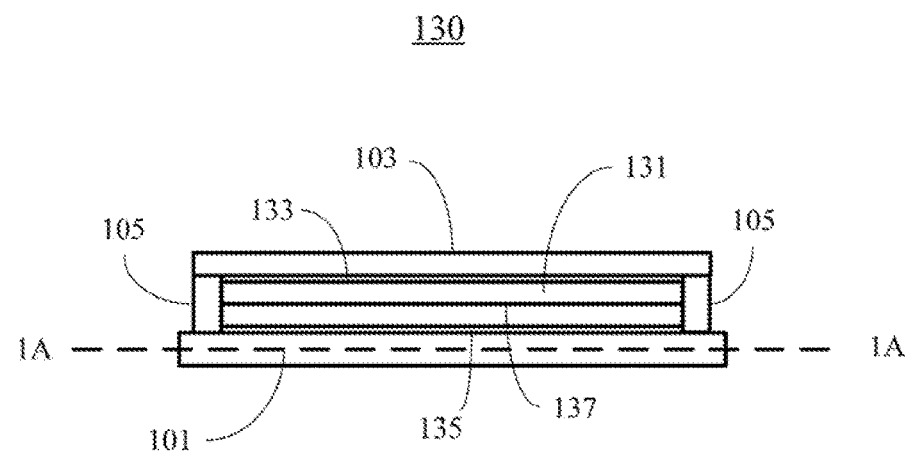
FIG. 2 is a cross-sectional view of the arm cast system of FIG. 1 taken along a LINE 1A-1A.

FIG. 2 is a cross-sectional view 130 of arm cast system 100 (FIG. 1) taken along LINE 1A-1A (FIG. 1). The relationship of pad 101, top portion 103 and ridge 105 is clearly illustrated. Ridge 105 is raised from pad and attached to 101 top portion 103 such that gap 131 is created in between pad 101 and top portion 103. As alluded to above in conjunction with FIG. 1, gap 131 is filled with a curable polymeric material, such as a radiation curable or energy-sensitive polymeric material or resin. The curable polymeric material or resin is preferably curable through exposure to a source of actinic radiation such as, but not limited to, ultraviolet (UV) light, or through exposure to an electrical current or voltage. The curable polymeric material that fills gap 131 is typically a liquid or gel that solidifies upon curing into a substantially rigid mass. The curable polymeric material may solidify as a result of various chemical reactions, including crosslinking and addition reactions. Within gap 131 is a mesh 137 that serves prevent cast 100 from stretching and thus strengthening cast 100 in much the same way that iron rebar placed within concrete strengths, or reinforces, the concrete.

A layer 133 positioned on gap 131 side of top portion 103 is reflective to the radiation that cures the energy-activated polymeric material that fills gap 131. Layer 133 serves to enable radiation passing through radiation access channels 117 and 119 to be distributed throughout gap 131, thus enabling all the curable polymeric material to be exposed to the radiation and thereby cured or hardened. A layer 135 on the gap 131 side of pad 101, like layer 133, also enables radiation transmitted through radiation access channels 117 and 119 to expose and thereby cure the curable polymeric material that fills gap 131.

In an alternative embodiment, cast system 100 does not include radiation access channels 117 or 119, or layers 133 or 135 but, rather, top portion 103 allows enough curing radiation from an external exposure unit to pass through the material of which it is constructed to quickly cure the energy-activated polymeric material.

In another embodiment, an electric current is introduced to the polymeric material by means of electrodes (not shown) implanted into gap 131 through either top portion 103 or ridge 105. This electric current causes the polymeric material to undergo a reaction by which it changes from a liquid or gel to a substantially rigid mass. In this manner, cast system 100 may be configured into a desired shape (see FIGS. 4 and 5) and subsequently (as through exposure to a suitable activation energy source to which the polymeric material is sensitive) turned into a hardened shell that functions as a medical cast.

Figure 3:
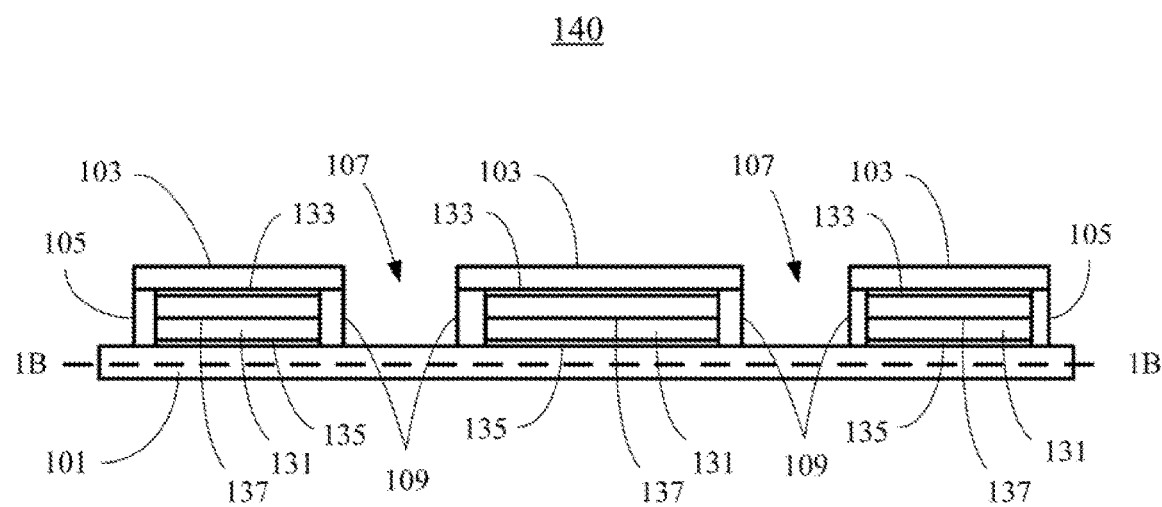
FIG. 3 is a cross-sectional view of the arm cast system of FIG. 1 taken along a LINE 1B-1B.

FIG. 3 is a cross-sectional view 140 of arm cast system 100 taken along LINE 1B-1B of FIG. 1. In view 140, pad 101, top portion 103, holes 107 and their respective ridges 109, ridge 105, layers 133 and 135 and radiation access channels are the same as described above in conjunction with FIG. 2. As explained above in conjunction with FIG. 1, holes 107 may extend through pad 101 rather than only through top portion 103. As explained above in conjunction with FIG. 2, gap 131 is filled with an energy-activated polymeric material so that, when cast system 100 is exposed to the particular UV or electrical energy to which the polymeric material is sensitive, system 100 turns into a hard shell that functions as a medical cast. Mesh 137 positioned within gap 131 provides extra strength to cast 100 once energy-activated polymeric material is hardened.

Figure 4:
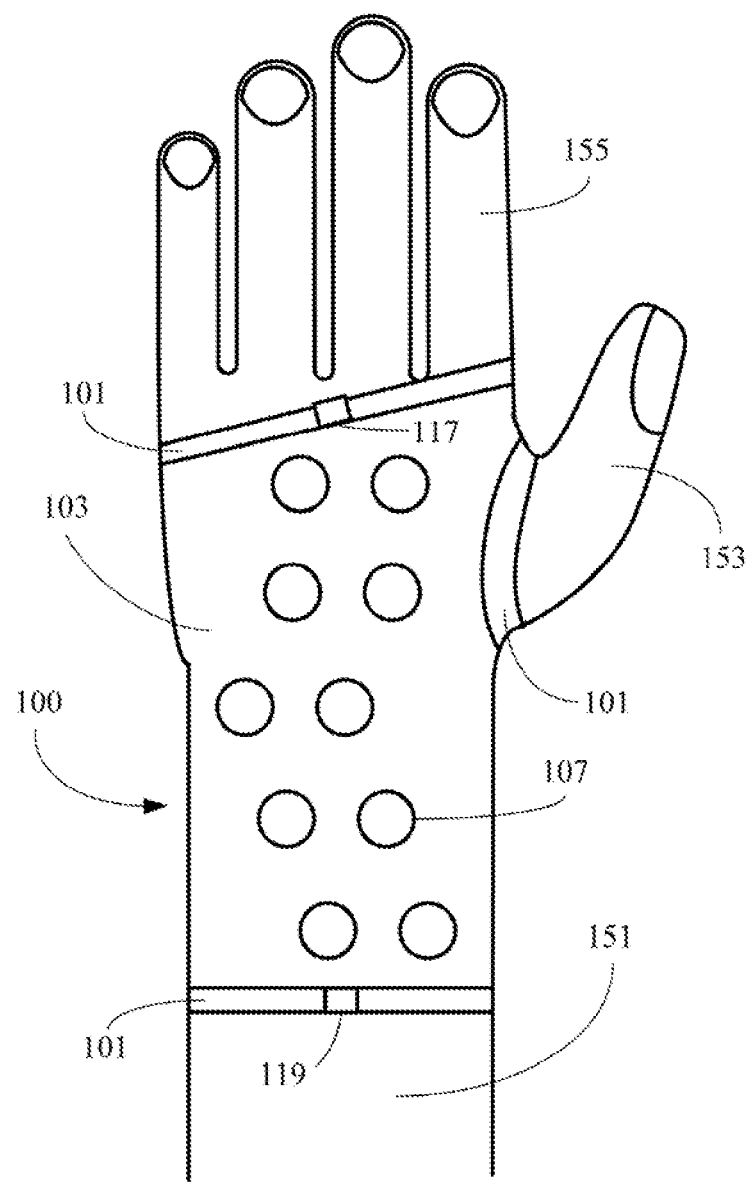
FIG. 4 is a top view of the arm cast system of FIG. 1 as applied to a patient's arm.

FIG. 4 is a top view illustrating the application of the arm cast system 100 of FIG. 1 to a patient's lower arm 151. FIG. 4 shows pad 101, top portion 103, holes 107 and radiation access channels 117 and 119, all of which are introduced above in conjunction with FIG. 1. Arm 151 includes a first metacarpal, or "thumb," 153 and a second metacarpal, or "index finger," 155. Cast system 100 is placed against arm 151 such that pad 101 is in contact with the skin of arm 151 and functions both to both cushion arm 151 from the rest of cast 100 and to insulate arm 100 form any heat that may be generated during the curing of the polymeric material encased in gap 131 (FIGS. 2 and 3). Cast system 100 is positioned upon arm 151 such that finger-like extension 115 (FIG. 1) wraps around arm 151 in between thumb 153 and index finger 155. The positioning of extension 115 between thumb 153 and index finger 155 may also be seen below in FIG. 5.

Figure 5:
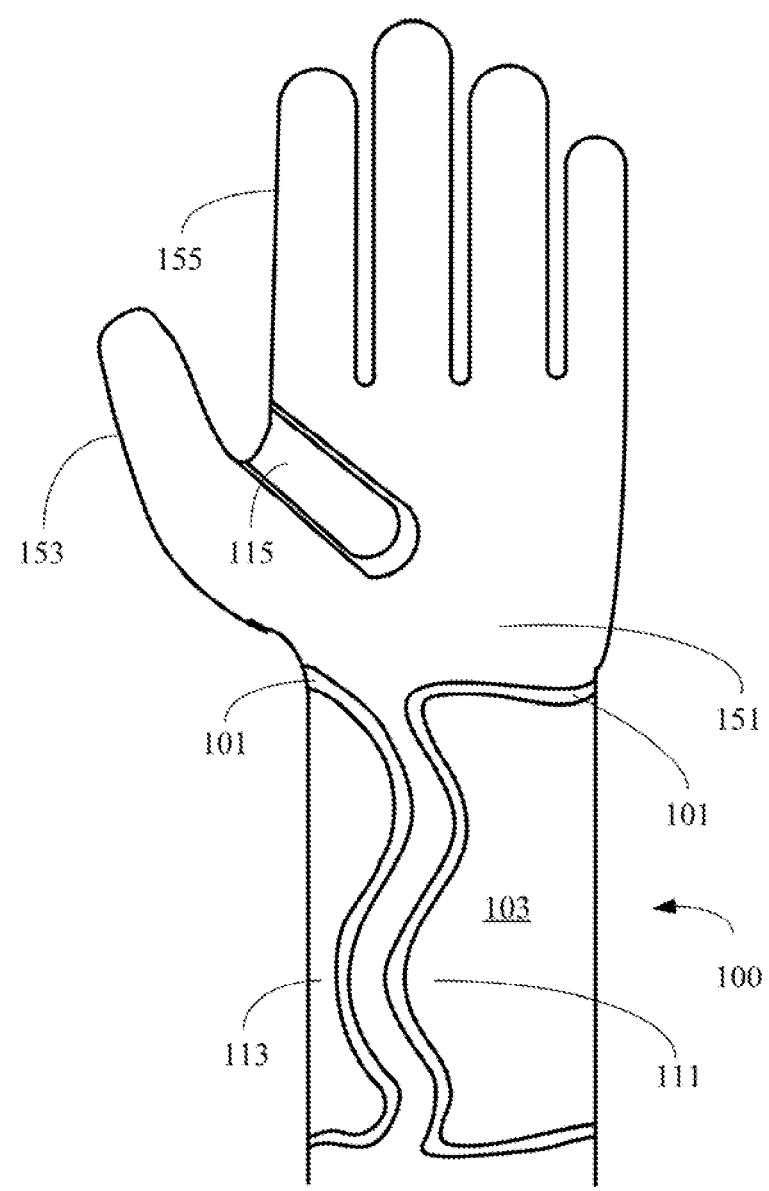
FIG. 5 is a bottom view of the arm cast system of FIGS. 1-4 as applied to the patient's arm.

FIG. 5 is a bottom view illustrating the application of arm cast system 100 of FIGS. 1-4 to a patient's lower arm 151 (FIG. 4). In this perspective, arm 151 is turned over so that the bottom side is up. Pad 101 (FIGS. 1-4) and top portion 103 (FIGS. 1-4) are wrapped around arm 151 such that convex portion 111 (FIG. 1) fits adjacent to corresponding convex portion 113 (FIG. 1). Extension 115 (FIG. 1) is positioned between thumb 153 (FIG. 4) and index finger 155 (FIG. 4).

In this embodiment, cast system 100 is positioned against arm 151 as shown in FIGS. 3 and 4 while the polymeric material that fills gap 131 (FIGS. 2 and 3) is still of a liquid or gel-like consistency. Once positioned against arm 151, cast system 100 is then exposed to the activating energy source to which it is sensitive, thus causing the polymeric material to harden. Thus, cast system 100 becomes a hard cast with padding material provided by pad 101, a protective shell provided by the hardened polymeric material that fills gap 131, and a cushion for the protective shell provided by top portion 103.

In an alternative embodiment, pad 101 is made of the same material as top portion 103 and a separate, more traditional padding is employed between cast system 100 and arm 151. In this embodiment, the polymeric material is simply encased in a single piece of material of the type used to construct top portion 103 above. The corresponding pad may be attached to the encasing material or applied separately as the cast is positions on the patient's arm.

Figure 6:
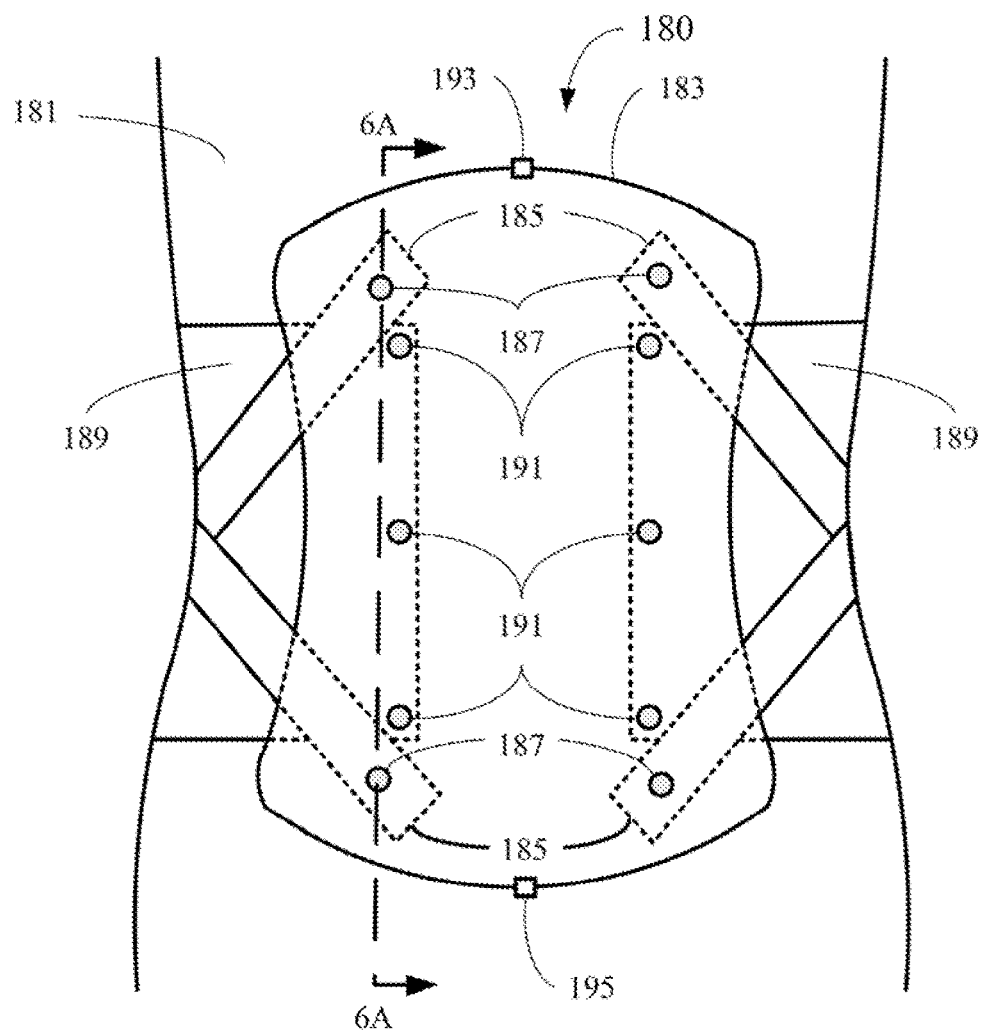
FIG. 6 is an illustration of an embodiment of a back brace made in accordance with the claimed subject matter.

FIG. 6 illustrates a portion of an exemplary back brace 180 that incorporates the claimed subject matter. In this example, brace 180 is shown installed on the posterior side of a human torso 181. Typically, a posterior back brace such as brace 180 is employed for either corrective or immobilizing purposes, and may have either a "short" or "long" configuration. Of course, it will be appreciated that the teachings herein may be applied to the construction of a brace having almost any purpose or configuration.

Brace 180 includes a posterior shell 183, adjustable straps 185 and elastic webbing 189. Adjustable straps 185 and elastic webbings 189 hold shell 183 in place against torso 181. Both straps 185 and webbings 189 fasten in the anterior, or front, (not shown) of torso 181. Dotted lines shown in the outline of straps 185 and webbing 189 indicate that those particular portions of straps 185 and webbing 189 are obscured from view by shell 183.

The teachings herein are equally applicable to an anterior shell brace (not shown), whether used on its own or in conjunction with a posterior brace such as brace 180. One with skill in the medical arts should recognize that there are many configurations suitable for securing a brace such as brace 180 to a torso or other body part. The particular brace configuration or body part application may vary from one implementation to the next.

Webbings 189 are attached to shell 183 at attachment points 191 by suitable fasteners, including, but not limited to, hook-and-loop type fasteners and repositionable adhesives. Straps 185 are likewise attached at attachment points 187 by suitable fasteners, which may be of the same or different type as the fasteners used to attach webbings 189 to shell 183. In one particular embodiment, an actinic radiation source is used to cure the polymeric material, and the fasteners that attach straps 185 and webbings 189 to shell 183 comprise a material that is transparent to the actinic radiation source. One skilled in the art will appreciate that a variety of plastics may be used for this purpose, and that the particular choice of plastic may depend on the actinic radiation source that is to be used to cure the polymeric material.

Brace 180 also includes one or more radiation access channels, in this example, radiation access channels 193 and 195. Radiation access channels 193 and 195 serve the same function with respect to brace 180 as radiation access channels 117 and 119 (FIGS. 1 and 4) serve with respect to cast 100 of FIGS. 1-5. Of course, as with cast system 100, there are alternative methods to ensure that shell 183 is properly cured.

In an alternative embodiment, shell 183 is cured without the fasteners, straps 185 and/or webbing 189 attached, and these items are added subsequent to curing. A dashed LINE 6A-6A is not part of brace 180 but rather indicates the position of a cut-away view 200 along a LINE 6A-6A with respect to brace 180. View 200 is illustrated below in conjunction with FIG. 7.

Figure 7:
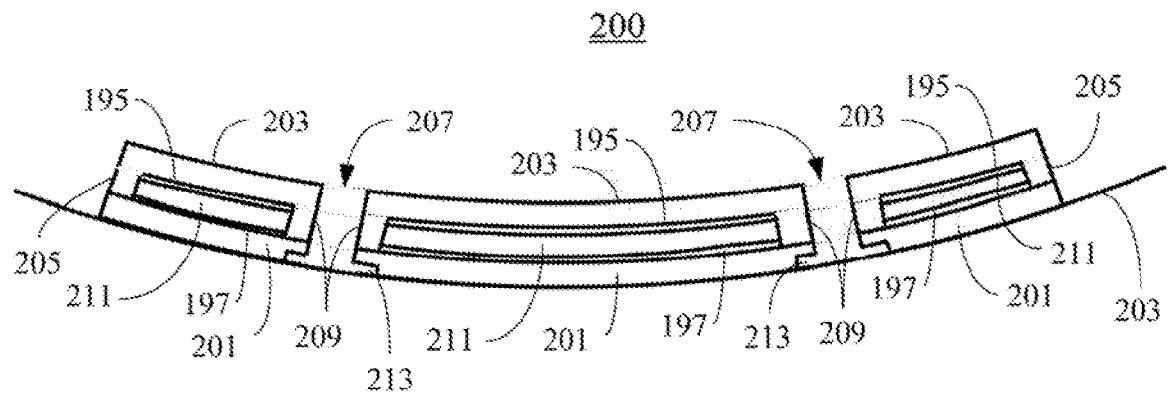
FIG. 7 is a cross-sectional view of the back brace of FIG. 6 taken along a LINE 6A-6A.

FIG. 7 is a cross-sectional view of brace 180 taken along LINE 6A-6A of FIG. 6 and depicting brace 180 positioned against a surface 203 of torso 181. The curvature of surface 203 may be equal, greater or less than the actual curvature of a human torso. Surface 203 is used only as an example of part of a human torso's topology, which may in fact be quite irregular. However, the teachings herein may be used to construct a brace having a shell (FIG. 7) that conforms to whatever shape torso 181 assumes, however irregular.

Like cast system 100 (FIGS. 1-5), brace 180 includes a pad 183 and an upper portion 203. Although view 200 appears to show several pieces to pad 201 and upper portion 203, preferably, pad 201 and top portion 203 are each of a singular construction and spaces 207 represent fastening points 187 (FIG. 5) through which fasteners (not shown) extend to attach straps 185 (FIG. 5) to shell 183 (FIG. 5), which in this illustration is represented by pad 201, top portion 203, holes 207 and so on. At the bottom of holes 207 are notches or recessions 209 that serve as space for heads (not shown) on fasteners 187 (FIG. 7) to fit so that fasteners 187 do not pull out of holes 207. Each notch 213 may extend entirely around the circumference of corresponding hole 207, or, in the alternative, may only be partially around hole 207 such that a fastener 187 with a matching head is prevented from rotating.

Pad 201 and top portion 203 are attached to each other at ridges 205 formed at the edges of top portion 203 and at ridges 209 formed on top portion 203 around holes 207. Similar ridges are formed in upper portion 203 around holes (not shown) at attachment points 191 (FIG. 7). Ridges 205 and 209 enable pad 201 and upper portion 203 to be attached to each other while leaving a gap 211 in between the portions of pad 201 and upper portion 203 that are not attached.

In an alternative embodiment, either or both ridges 205 and 209 are formed on pad 201 rather than upper portion 203. Further, pad 201 and upper portion 203 may not include ridges 205 and 209 but rather their function, i.e., attaching and creating gap 211 between pad 201 and upper portion 203, may be performed by a separate piece of suitable material in the form of one or more gaskets. In another embodiment, pad 201 is constructed of the same material as top portion 101, both of which are a single piece of material molded to create a gap such as gap 211. In this embodiment, a separate piece of material, either attached or unattached, is employed as padding.

Like gap 131 of cast system 100, gap 211 is filled with an energy-activated polymeric material. Thus, for example, the polymeric material may be curable through exposure to a particular type of energy such as, but not limited to, UV light or an electrical current. In the example of UV light, the energy-activated polymeric material that fills gap 211 has a liquid or gel-like consistency when placed into gap 211. When brace shell 180 is exposed to a UV light source, the polymeric material in gap 211 hardens or cures, forming a permanent, custom-fitted shell. Both UV curable and electrically curable polymeric materials can be employed in gap 211 that are curable relatively quickly.

Figure 8:
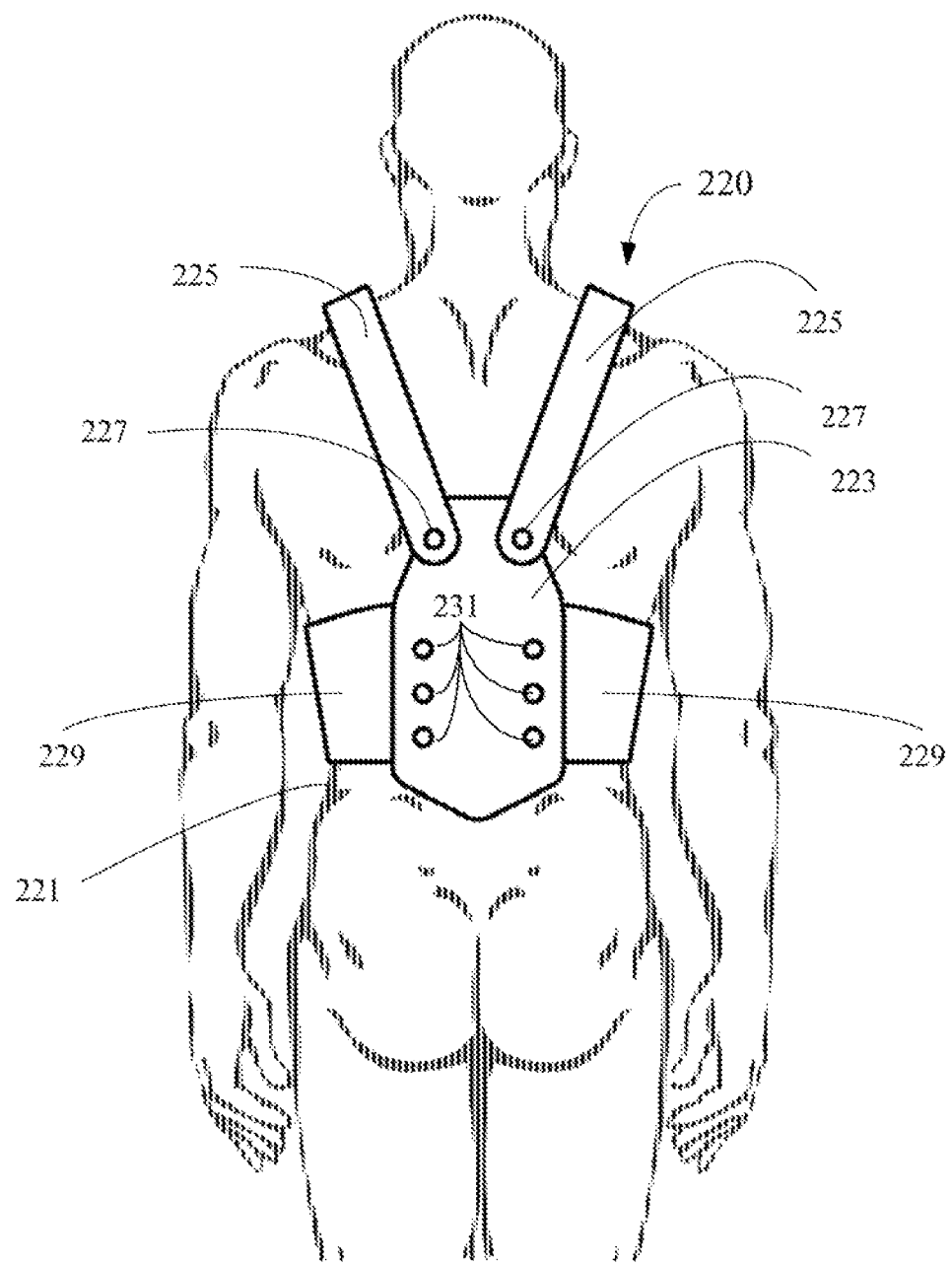
FIG. 8 is an alternative embodiment of a back brace made in accordance with the claimed subject matter.

FIG. 8 is an alternative embodiment of a back brace 220 made in accordance positioned against a surface 223 of torso 221. The curvature of surface 223 may be equal, greater or less than the actual curvature of a human torso. Surface 223 is used only as an example of part of a human torso's topology, which may in fact be quite irregular. However, the teachings herein may be used to construct a brace having a shell (FIG. 7) that conforms to whatever shape torso 201 assumes, however irregular.

In this example, brace 220 is shown installed on the posterior side of a human torso 221. Typically, a posterior back brace such as brace 220 is employed for either corrective or immobilizing purposes, and may have either a "short" or "long" configuration. Of course, it will be appreciated that the teachings herein may be applied to the construction of a brace having almost any purpose or configuration.

Brace 220 includes a posterior shell 223, adjustable straps 225 and elastic webbing 229. Elastic straps attach to shell 223 at attachment points 231. Adjustable straps 225 and elastic webbings 229 hold shell 223 in place against torso 221. Both straps 225 and webbings 229 may fasten in the anterior, or front, (not shown) of torso 221.

The teachings herein are equally applicable to an anterior shell brace (not shown), whether used on its own or in conjunction with a posterior brace such as braces 180 and 220. One with skill in the medical arts should recognize that there are many configurations suitable for securing a brace such as braces 180 and 220 to a torso or other body part. The particular brace configuration or body part application may vary from one implementation to the next.

Webbings 229 are attached to shell 223 at attachment points 231 by suitable fasteners, including, but not limited to, hook-and-loop type fasteners and repositionable adhesives. Straps 225 are likewise attached at attachment points 227 by suitable fasteners, which may be of the same or different type as the fasteners used to attach webbings 229 to shell 223. In one particular embodiment, an actinic radiation source is used to cure the polymeric material, and the fasteners that attach straps 225 and webbings 229 to shell 223 comprise a material that is transparent to the actinic radiation source. One skilled in the art will appreciate that a variety of plastics may be used for this purpose, and that the particular choice of plastic may depend on the actinic radiation source that is to be used to cure the polymeric material.

Various curable polymeric materials may be used in the devices and methodologies disclosed herein. These include, but are not limited to, radiation curable materials based on acrylates, epoxides, urethanes, urea-acrylates, urethane-acrylates, epoxy-acrylates, polyether acrylates, polyester acrylates, urethane epoxides, silicone acrylates, acrylate-thiol-ene systems, ethylene copolymer elastomer compositions, acrylate rubber compositions, nitrile rubber compositions, fluoroelastomer compositions, chlorinated elastomer compositions, and silicone polymers. When the curable polymeric materials comprise photocurable polymers, they may be employed with appropriate catalysts, photoinitiators or crosslinking agents. Thus, for example, some epoxide-based systems may be cured through crosslinking reactions based on photoinitiated acid formation (using, for example, photo-acid generators based on aromatic diazonium salts, aromatic iodonium salts and triarylsulfonium salts), photoinitiated base formation (using, for example, photo-base generators bearing acyloxyimino groups), or photogenerated amines (using, for example, oxime-urethane derivatives). Photocurable polymeric materials may also be formed from various multifunctional monomers.

The curable polymeric materials employed in the devices and methodologies described herein may be cured through a variety of means. Thus, for example, these materials may be cured through irradiation with actinic energy rays, such as UV radiation (both short and long wavelength UV radiation), IR radiation, electron rays, and X-rays. Suitable sources of actinic radiation may include mercury lamps of low, medium, high, or super-high pressure, metal halide lamps, xenon lamps, and carbon arc lamps. These materials may also be cured through exposure to various laser sources, including semiconductor lasers, argon lasers and He—Cd lasers, or through exposure to ionizing radiation, such as alpha-rays, beta-rays, gamma-rays, neutron beams, X-rays and accelerated electron rays. In some embodiments, one or more layers of materials that reflect or adsorb the radiation emitted by the radiation source may be disposed between the curable polymeric material and the patient to protect the patient from any harmful effects associated with exposure to the emitted radiation.

The curable polymeric materials employed in the devices and methodologies described herein may have various components as are known to the art. These include, in addition to the curable polymers themselves, various crosslinking agents, activators, photoinitiators, fillers, plasticizers, pigments, dyes, solvents, cosolvents, stabilizers, surfactants, metallocene compounds (these may have various aromatic electron system ligands), and the like.

The polymer may have chopped, woven or braided reinforcement material, such as fiberglass or carbon fiber, distributed within, on top of or below in a random or patterned orientation. The polymer may be can be cured to form a solid sheet or a scaffold or lattice type of rigid support or a combination there of.

While various embodiments of the application have been described, it will be apparent to those of ordinary skill in the art that many more embodiments and implementations are possible that are within the scope of this invention. Accordingly, the invention is not to be restricted except in light of the attached claims and their equivalents.

I claim:

1. A formable cast, comprising:
a padding;
an outer shell, comprising a planar sheet with opposing edges, wherein the opposing edges of the outer shell have a concave portion and a convex portion, respectively, that fit into each other when the outer shell is adapted to wrap around a body part;
a ridge disposed along the perimeter of the outer shell, wherein the ridge, the outer shell and the padding define an interior space; and
a curable polymeric material disposed in the interior space,
wherein the curable polymeric material is a liquid or gel in a first phase and in a first shape and, upon exposure to an energy source for curing the curable polymeric material, cures to a hardened material in a second phase, while remaining in the first shape.

2. The cast of claim 1, wherein the energy source is actinic radiation.

3. The energy-sensitive, formable cast of claim 1, wherein the energy source is ultraviolet (UV) radiation.

4. The cast of claim 1, wherein the outer shell is transparent to the energy source for curing the curable polymeric material.

5. The cast of claim 1, further comprising one or more radiation access ports for exposing the curable polymeric material to the energy source for curing the curable polymeric material.

6. The cast of claim 5, further comprising a reflective layer on the interior space side of the pad and the outer shell for reflecting radiation corresponding to the energy source to facilitate a distribution of the energy source throughout the interior space.

7. The cast or claim 1, wherein the padding is adapted to cushioning the skin of a patient from the outer shell.

8. The cast of claim 1, wherein the padding is adapted to insulate the skin from heat produced during the curing of the curable polymeric material.

9. The cast of claim 1, further comprising a mesh positioned within the curable polymeric material.

10. An energy-activated, formable cast, comprising:
a pad adapted to cushioning the cast against the skin of a patient;
an outer shell, comprising a planar sheet with opposing edges, wherein the opposing edges of the outer shell have a concave portion and a convex portion, respectively, that fit into each other when the outer shell is adapted to wrap around a body part;
a ridge disposed along the perimeter of the outer shell, wherein the ridge connect the pad and the outer shell to create a gap therebetween; and
an energy-sensitive polymeric material that fills the gap, wherein the energy-sensitive polymeric material is formable when placed into the gap and hardens when exposed to an energy source to which the energy-sensitive polymeric material is sensitive such that the outer shell is adapted to conform to the body part of the patient when the energy-sensitive polymeric material is formable and provide support to the body part once the energy-sensitive polymeric material has hardened.

11. The energy-sensitive, formable cast of claim 10, wherein the energy source is ultraviolet (UV) light.

12. The energy-sensitive, formable cast of claim 10, wherein the energy source is an electric current.

13. The energy-sensitive, formable cast of claim 10, further comprising one or more radiation access ports for transmitting the energy source to the energy-sensitive polymeric material.

14. The energy-sensitive, formable cast of claim 10, further comprising a mesh positioned within the energy-sensitive polymeric material.

15. The energy-sensitive, formable cast of claim 10, further comprising a reflective layer on the gap side of the pad and the outer shell for reflecting the energy source to facilitate a distribution of the energy source throughout the gap.

16. The energy-sensitive, formable cast of claim 10, wherein the pad is made of a breathable, resilient material.

17. The energy-sensitive, formable cast of claim 10, wherein the body part is the lower arm.

18. The energy-sensitive, formable cast of claim 10, wherein the particular body part is the leg.

\* \* \* \* \*